Sept. 29, 1959 G. MERRILL Plant Pat. 1,869
PEACH TREE
Filed July 7, 1958
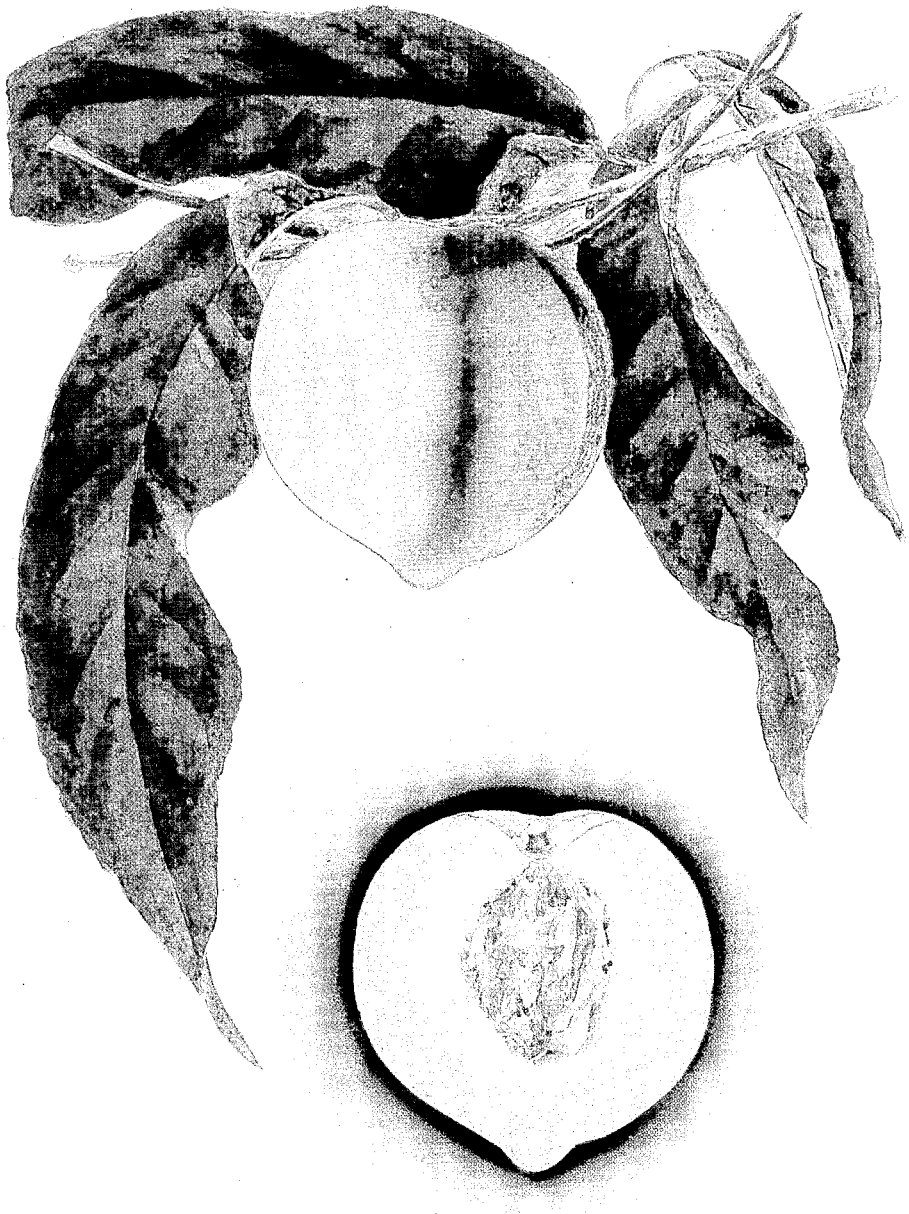
WITNESS
Addison E Avery
INVENTOR
GRANT MERRILL
HUEBNER & WORREL
BY Richard M. Worrel ATTY.

United States Patent Office

Plant Pat. 1,869
Patented Sept. 29, 1959

1,869

PEACH TREE

Grant Merrill, Red Bluff, Calif.

Application July 7, 1958, Serial No. 747,107

1 Claim. (Cl. 47—62)

This invention relates to a new and distinct variety of peach tree which bears very highly colored peaches, which are firm yellow fleshed, some times freestone, of good size, fine shipping quality, with trees of good production and with a mid-season blooming season.

A distinguishing characteristic of the instant variety is that it ripens in Red Bluff, California, about seven days ahead of Redhaven (unpatented) and about ten days later than Merrill Gemfree (Plant Patent No. 1,409).

In comparison with Merrill Gemfree (Plant Patent No. 1,409), which it most nearly resembles, the fruit of the instant variety ripens about ten days later and has a brighter red skin color. As compared with Redhaven (unpatented), the instant variety has considerably more red skin color, is more round in shape, and ripens about seven days earlier.

I originated the variety on my farm near Red Bluff, Tehama County, California.

The July Elberta of Plant Patent No. 15 was crossed with a peach tree resulting from a cross between the unpatented J. H. Hale and Red Bird varieties and a seed resulting from the open pollination of the resulting progeny was germinated to produce the instant variety. (July Elberta, Plant Patent No. 15 × (J. H. Hale, unpatented × Red Bird, unpatented) × Open.)

In the fall of 1956, several trees planted the previous year were budded to this new variety on my farm at Red Bluff, Tehama County, California, and the trees fruited in June, 1958. The fruit and tree characteristics proved identical to those of the original seedlings. Also several trees of Merrill June (Plant Patent No. 869) were grafted in the spring of 1956 to this variety at my farm near Lamont, Kern County, California. These trees fruited in June, 1958 and the fruit and tree characteristics proved to be identical with the original seedling.

In the drawing, the fruit of the subject variety is shown in elevation together with twigs and leaves and an additional fruit is shown divided on its suture plane with its stone exposed.

Referring now more specifically to the promological details of this new and distinct variety of peach tree, the following is an outline description thereof; all major color plate identifications being by reference to either Maerz and Paul Dictionary of Color, except where indicated, to the British Horticultural Chart of the British Color Council:

*Tree*

Medium size, medium vigor, medium upright, medium dense, vase formed by pruning, hardiness unknown, productive, regular bearer.

Trunk: Medium stocky, medium shaggy.

Branches: Grey and shaggy on older branches, more smooth and brown on younger branches. Lenticels—medium numerous, medium size.

Leaves: (Selected from midportion of vigorous unbranched terminal shoots 18" to 24" long).

*Length.*—6¾" to 7⅞", average 7½".

*Width.*—1⅜" to 2", average 1 13/16". Large in size, lanceolate, tip acuminate, medium thin.

*Color* (Using the British Horticulture Chart of the British Color Council).—Upper surface, Spinach Green, Plate 187, No. 0960. Under surface, Spinach Green, Plate 187, No. 0960/3. Midrib on underside, Plate 90, No. 663/2.

*Class* (Meader and Blake: Proceedings Am. Soc. Hor. Sc. vol. 27, page 206).—2 and 3. Width-length ratio .24. Apex angle 30° to 37½°, average 33° Base angle 75° to 95°, average 87°.

*Margin.*—Crenate.

*Petiole.*—Medium long, medium thick.

*Glands.*—Two to six, average 3 or 4. Alternate, medium size, reniform, green, on lower part of leaf and upper part of petiole.

*Stipules.*—On new growth, falling off early.

Flower buds: Hardiness unknown, medium size medium length, truncate to obtuse, plump, free, pubescent.

Flowers: Midseason, small, pink, pollen abundant.

*Fruit*

Maturity when described, eating ripe.

Size: Variable.

*Axial Diameter.*—2½" to 3", average 2 11/16".

*Transverse in suture plane.*—2 9/16" to 2⅞", average 2 11/16".

*At right angles to suture plane.*—2 5/16" to 2⅞", average 2½".

Form: Globose to slightly ovoid.

*Suture.*—Distinct, shallow, extends from base but discontinues at apex, some have a slight depression beyond the pistil point.

*Ventral surface.*—Rounded, lips if any, unequal.

*Cavity.*—Abrupt, elongated in suture plane, with suture showing on one or both sides. Depth ½" to ⅝", average 17/32". Breadth, ½" to ⅝", average 9/16". Markings—yellow under color, blush extending into cavity on most.

*Base.*—Truncate.

*Apex.*—Cuspidate to mucronate, pistil point apical.

*Stem.*—¼" to ½", somewhat short tending to produce a crease in the base of some of the fruit. Diameter average ⅛".

*Skin.*—Medium thick, medium tender, tenacious to flesh, tendency to crack, none. Down—scant, short, does not roll up when rubbed. Color—under color, yellow (10–L–7) to (11–L–9), blush in the form of general blush, with some striping fairly heavy to almost covering the entire surface. Color (3–L–10) to (6–L–6).

Flesh: Color from yellow (9–K–4) near skin to (9–K–8), some color in flesh (9–L–11). The red is mottled throughout on some fruit, some fruit with little red.

*Surface of pit cavity.*—Yellow.

*Amygadalin.*—Scant.

*Juice.*—Moderate.

*Texture.*—Firm, meaty to tough.

*Fibers.*—Few and tender.

*Ripens.*—Evenly.

*Flavor.*—Mild, delicate.

*Aroma.*—Distinct.

*Eating quality.*—Fair to good.

*Adherence to stone.*—Cling when firm, part free on ripening.

Stone: Adheres to the flesh over the entire surface when firm ripe, becomes partly freestone on softening.

*Fibers.*—Short.

*Size.*—Small, average length 23/64", average width 31/32", average thickness 3/4".

*Form.*—Ovoid to obovate.

*Base.*—Oblique.

*Hilum.*—Oval to irregular.

*Apex.*—Cuspidate.

*Sides.*—Mostly equal, some unequal, flattened toward base on some.

*Ventral edge.*—Thick without wing toward base.

*Dorsal edge.*—Full with short diagonal grooves.

*Color.*—Tan (10–A–7).

*Tendency to split.*—But little.

Use: Market, local, dessert, culinary and long distance shipping.

Keeping quality: Good.

Shipping quality: Good.

*General notes*

The tree and its fruit herein described may vary some due to climatic and soil conditions under which the variety may be grown, and the method of growing, including fertilizing, pruning, thinning, the pest and diseases present on the tree, and other causes.

Having illustrated and described my new discovery, I claim:

A new and distinct variety of peach tree substantially as shown and described characterized by the production of highly colored fruit resembling the Merrill Gemfree (Plant Patent No. 1,409) but being of brighter red blush and ripening approximately ten days later than the Gemfree and approximately ten days earlier than the Redhaven (unpatented), the fruit also being characterized by firm, yellow flesh, good size and by being clingstone when firm but becoming partly freestone when soft ripe.

No references cited.